(12) United States Patent
Martchenko et al.

(10) Patent No.: US 9,439,876 B2
(45) Date of Patent: Sep. 13, 2016

(54) METHOD OF TREATING MICROBIAL INFECTIONS

(71) Applicant: Keck Graduate Institute of Applied Life Sciences, Claremont, CA (US)

(72) Inventors: Mikhail Martchenko, Claremont, CA (US); Kevin Jee Kim, Downey, CA (US)

(73) Assignee: KECK GRADUATE INSTITUTE OF APPLIED LIFE SCIENCES, Claremont, CA (US)

(*) Notice: Subject to any disclaimer, the term of this patent is extended or adjusted under 35 U.S.C. 154(b) by 209 days.

(21) Appl. No.: 14/153,885

(22) Filed: Jan. 13, 2014

(65) Prior Publication Data

US 2015/0196499 A1    Jul. 16, 2015

(51) Int. Cl.
  *A61K 31/131*    (2006.01)
  *A61K 45/06*    (2006.01)
  *A01N 33/04*    (2006.01)
  *C02F 1/50*    (2006.01)

(52) U.S. Cl.
  CPC .............. *A61K 31/131* (2013.01); *A01N 33/04* (2013.01); *A61K 45/06* (2013.01); *C02F 1/50* (2013.01); *C02F 2303/04* (2013.01)

(58) Field of Classification Search
  CPC ..... A61K 31/131; A61K 45/06; A61N 33/04
  See application file for complete search history.

(56) References Cited

PUBLICATIONS

Ghannoum, "Antifungal Agents: Mode of Action, Mechanisms of Resistance, and Correlation of These Mechanisms with Bacterial Resistance", Clinical Microbiology Reviews, Oct. 1999, p. 501-517.*
Behrman, RE WJ; "FDA regulations for drug development" Science 329: 33; (2010) (On Order).
Chong, CR et al.; "A clinical drug library screen identifies astemizole as an antimalarial agent"; Nat Chem Biol 2: 415-416; (2006) (On Order).
De Prijck, K et al.; "Inhibition of Candida albicans biofilm formation by antimycotics released from modified polydimethyl siloxane"; Mycopathologia 169: 167-174; (2010) (On Order).
Elin, RJ et al.; "Effect of pH and iron concentration on growth of Candida albicans in human serum"; J Infect Dis 127: 705-708; (1973) (On Order).
Fisher, JF et al.; "Candida urinary tract infections—treatment"; Clin Infect Dis 52 Suppl 6: 5457466; (2011) (On Order).
Fujitani, S et al.; "Ethnicity and other possible risk factors for candidemia at 3 tertiary care university hospitals in Hawaii"; Infect Control Hosp Epidemiol 27: 1261-1263; (2006) (On Order).
Gale, GR et al.; "Pharmacology of captan: biochemical effects with special reference to macromolecular synthesis" Toxicol Appl Pharmacol 18: 426-441; (1971) (On Order).

Gow, NA et al.; "Candida albicans morphogenesis and host defense: discriminating invasion from colonization"; Nat Rev Microbiol 10: 112-122; (2012) (On Order).
Grossman, LI; "Evaluation of antifungal agents for endodontic use"; J Dent Res 46: 215-217; (1967) (On Order).
Hendry, AT et al.; "Factors affecting serum inhibited growth of Candida albicans and Cryptococcus neoformans"; Sabouraudia 7: 219-229; (1969) (On Order).
Hernandez Molina, JM et al.; In vitro activity of nitroxoline against clinical isolates of *Candida* species. Mycoses 34: 323-325; (1991) (On Order).
Homann, OR et al.; "A phenotypic profile of the Candida albicans regulatory network"; PLoS Genet 5: el000783; (2009) (On Order).
Ichikawa, T. et al; "The enhancement effect of three sugar alcohols on the fungicidal effect of benzethonium chloride toward Candida albicans"; J Dent 36: 965-968; (2008) (On Order).
King, RD et al.; "Transferrin, iron, and dermatophytes"; I. Serum dematophyte inhibitory component definitively identified as unsaturated transferrin. J Lab Clin Med 86: 204-212; (1975) (On Order).
Kohler, GA et al.; "The functional basis of mycophenolic acid resistance in Candida albicans IMP dehydrogenase"; J Biol Chem 280: 11295-11302; (2005) (On Order).
Kot, EJ et al.; "An alternate respiratory pathway in Candida albicans"; Antonie Van Leeuwenhoek 42: 33-48; (1976) (On Order).
Lovgren, T et al.; "In vitro sensitivity of Trichomonas vaginalis and Candida albicans to chemotherapeutic agents"; Acta Pathol Microbiol Scand B 86B: 155-158; (1978) (On Order).
Lu, Q et al.; "EST-based genome-wide gene inactivation identifies ARAP3 as a host protein affecting cellular susceptibility to anthrax toxin"; Proc Natl Acad Sci U S A 101: 17246-17251; (2004) (On Order).
Molepo, J. et al.; "Clade-related phenotypic switching among fluconazole resistant Candida albicans isolates"; SADJ 67: 326-328; (2012) (On Order).
Nash, JD et al.; "Effect of fluvastatin and pravastatin, HMG-CoA reductase inhibitors, on fluconazole activity against Candida albicans"; J Med Microbiol 51: 105-109; (2002) (On Order).
Nilakantan, R. et al.; "A novel approach to combinatorial library design"; Comb Chem High Throughput Screen 5: 105-110; (2002) (On Order).
Nobile, CJ et al.; "Regulation of cell-surface genes and biofilm formation by the C. albicans transcription factor Bcr1p"; Curr Biol 15: 1150-1155; (2005) (on Order).
Noble, SM et al.; "Systematic screens of a Candida albicans homozygous deletion library decouple morphogenetic switching and pathogenicity"; Nat Genet 42: 590-598; (2010) (On Order).
Norice, CT et al.; Requirement for Candida albicans Sun41 in biofilm formation and virulence. Eukaryot Cell 6: 2046-2055; (2007) (on Order).
Odds, FC et al.; "Antifungal agents: mechanisms of action"; Trends Microbiol 11: 272-279; (2003) (On Order).

(Continued)

*Primary Examiner* — Sahar Javanmard
(74) *Attorney, Agent, or Firm* — Lewis Roca Rothgerber Christie LLP

(57) ABSTRACT

Methods of inhibiting or preventing the proliferation of a fungus and/or a bacteria in a living organism, in water, in air, and/or on surfaces, include administering or providing a therapeutic amount or an effective amount of an antimicrobial composition including Octodrine.

12 Claims, 13 Drawing Sheets
(12 of 13 Drawing Sheet(s) Filed in Color)

(56) References Cited

PUBLICATIONS

Omura, Y. et al.; "Caprylic acid in the effective treatment of intractable medical problems of frequent urination, incontinence, chronic upper respiratory infection, root canalled tooth infection, ALS, etc., caused by asbestos & mixed infections of Candida albicans, Helicobacter pylori & cytomegalovirus with or without other microorganisms & mercury"; Acupunct Electrother Res 36: 19-64; (2011) (On Order).
Perlroth, J. et al.; "Nosocomial fungal infections: epidemiology, diagnosis, and treatment"; Med Mycol 45: 321-346; (2007) (On Order).
Rauceo, JM et al.; Regulation of the Candida albicans cell wall damage response by transcription factor Sko1 and PAS kinase Psk1; Mol Biol Cell 19: 2741-2751; (2008) (On Order).
Shukla, S. et al.; "Disulfiram is a potent modulator of multidrug transporter Cdr1p of Candida albicans"; Biochem Biophys Res Commun 322: 520-525; (2004) (On Order).
Siles, SA. et al.; "High-Throughput Screening of a Collection of Known Pharmacologically Active Small Compounds for Identification of Candida albicans Biofilm Inhibitors"; Antimicrob Agents Chemother 57: 3681-3687; (2013) (On Order).
Vandenbosch, D. et al.; "Phytosphingosine-l-phosphate is a signaling molecule involved in miconazole resistance in sessile Candida albicans cells"; Antimicrob Agents Chemother 56: 2290-2294; (2012) (On Order).
Vandeputte, P. et al.; "Antifungal resistance and new strategies to control fungal infections"; Int I Microbic.' 2012: 713687; (2012) (On Order).
Wachtler, B. et al.; "Candida albicans adhesion to and invasion and damage of vaginal epithelial cells: stage-specific inhibition by clotrimazole and bifonazole"; Antimicrob Agents Chemother 55: 4436-4439; (2011) (On Order).
Wilson, LS et al.; "The direct cost and incidence of systemic fungal infections"; Value Health 5: 26-34; (2002) (On Order).
Behrman, Rachel E. et al.; "FDA Regulations for Drug Development"; Science; vol. 329; Jul. 2, 2010; p. 33.
Chong, Curtis R. et al.; "A clinical drug library screen identifies astemizole as an antimalarial agent"; Nat Chem Biol; vol. 2; No. 8; Aug. 2006; pp. 415-416.
De Prijck, Kristof et al ; "Inhibition of Candida albicans Biofilm Formation by Antimycotics Released from Modified Polydimethyl Siloxane"; Mycopathologia; 169; 2010; pp. 167-174.
Elin, Ronald J. et al.; "Effect of pH and Iron Concentration on Growth of Candida albicans in Human Serum"; The Journal of Infectious Diseases; vol. 127; No. 6; Jun. 1973; pp. 705-708.
Fisher, John F. et al.; "Candida Urinary Tract Infections-Treatment"; CID; Suppl. 6; 2011; 52; pp. S457-S466.
Fujitani, Shigeki et al.; "Ethnicity and Other Possible Risk Factors for Candidemia at 3 Tertiary Care University Hospitals in Hawaii"; Infection Control and Hospital Epidemiology; vol. 27; No. 11; Nov. 2006; pp. 1261-1263.
Gale, Glen R. et al.; "Pharmacology of Captan: Biochemical Effects with Special Reference to Macromolecular Synthesis"; Toxicology and Applied Pharmacology; 18; 1971; pp. 426-441.
Gow, Neil A. R. et al.; "Candida albicans morphogenesis and host defense: discriminating invasion from colonization"; Nature Reviews: Microbiology; vol. 10; Feb. 2012; pp. 112-122.
Grossman, Louis I.; "Evaluation of Antifungal Agents for Endodontic Use"; J Dent Res; vol. 46; No. 1; 1967; pp. 215-217.
Hendry, A. T. et al.; "Factors affecting serum inhibited growth of Candida albicans and Cryptococcus neoformans"; Sabouraudia 7; 1969; pp. 219-229.
Hernandez Molina, J. M. et al.; "In vitro activity of nitroxoline against clinical isolates of Candida species"; Mycoses 34; 1991; pp. 323-325.
Homann, Oliver Ret al.; "A Phenotypic Profile of the Candida albicans Regulatory Network"; PLoS Genetics; vol. 5; Issue 12; Dec. 2009; e1000783; 12pp.
Ichikawa, T. et al; "The enhancement effect of three sugar alcohols on the fungicidal effect of benzethonium chloride toward Candida albicans"; Journal of Dentistry; 36; 2008; pp. 965-968.
King, Robert D. et al.; "Transferrin, iron, and dermatophytes. I. Serum dematophyte inhibitory component definitively identified as unsaturated transferrin"; J Lab Clin Med; 86; 1975; pp. 204-212.
Köhler, Gerwald A. et al.; "The Functional Basis of Mycophenolic Acid Resistance in Candida albicans IMP Dehydrogenase"; J Biol Chem; vol. 280; No. 12; Mar. 25, 2005; pp. 11295-11302.
Kot, E. J. et al.; "An alternate respiratory pathway in Candida albicans"; Antonie Van Leeuwenhoek; 42; 1976; pp. 33-48.
Lövgren, Timo et al.; "In vitro sensitivity of Trichomonas vaginalis and Candida albicans to chemotherapeutic agents"; Acta Path. Microbiol. Scand.; Sect. B; 86; 1978; pp. 155-158.
Lu, Quan et al.; "EST-based genome-wide gene inactivation identifies ARAP3 as a host protein affecting cellular susceptibility to anthrax toxin"; PNAS; vol. 101; No. 49; Dec. 7, 2004; pp. 1724617251.
Molepo, Julitha; "Clade Related Antifungal Resistance Among South African Candida albicans Isolates"; Thesis (PhD (Microbiological Pathology)—University of Limpopo (Medunsa Campus); 2010; 250pp.
Nash, James D. et al.; "Effect of fluvastatin and pravastatin, HMG-CoA reductase inhibitors, on fluconazole activity against Candida albicans"; J. Med. Microbiol .; vol. 51; 2002; pp. 105-109.
Nilakantan, Ramaswamy et al.; "A Novel Approach to Combinatorial Library Design"; Combinatorial Chemistry & High Throughput Screening; 5; 2002; pp. 105-110.
Nobile, Clarissa J. et al.; "Regulation of Cell-Surface Genes and Biofilm Formation by the C. albicans Transcription Factor Bcr1p"; Current Biology; vol. 15; Jun 21, 2005; pp. 1150-1155.
Noble, Suzanne M. et al.; "Systematic screens of a Candida albicans homozygous deletion library decouple morphogenetic switching and pathogenicity"; Nature Genetics; vol. 42; No. 7; Jul. 2010; pp. 590-598.
Norice, Carmelle T. et al.; "Requirement for Candida albicans Sun41 in Biofilm Formation and Virulence"; Eukaryotic Cell; vol. 6; No. 11; Nov. 2007; pp. 2046-2055.
Odds, Frank C. et al.; "Antifungal agents: mechanisms of action"; Trends in Microbiology; vol. 11; No. 6; Jun. 2003; pp. 272-279.
Omura, Yoshiaki et al.; "Caprylic acid in the Effective Treatment of Intractable Medical Problems of Frequent Urination, Incontinence, Chronic Upper Respiratory Infection, Root Canalled Tooth Infection, ALS, etc., Caused by Asbestos & Mixed Infections of Candida albicans, Helicobacter pylori & Cytomegalovirus With or Without Other Microorganisms & Mercury"; Acupuncture & Electro-Therapeutics Res., Int. J.; vol. 36; 2011; pp. 19-64.
Paul, T. R. et al.; "Effect of iron depletion on cell-wall antigens of Candida albicans"; J. Med. Microbiol.; vol. 28; 1989; pp. 93-100.
Perlroth, Joshua et al.; "Nosocomial fungal infections: epidemiology, diagnosis, and treatment"; Medical Mycology; 45; Jun. 2007; pp. 321-346.
Rauceo, Jason M. et al.; "Regulation of the Candida albicans Cell Wall Damage Response by Transcription Factor Sko1 and PAS Kinase Psk1"; Molecular Biology of the Cell; vol. 19; Jul. 2008; pp. 2741-2751.
Shukla, Suneet et al.; "Disulfiram is a potent modulator of multidrug transporter Cdr1p of Candida albicans"; Biochemical and Biophysical Research Communications; 322; 2004; pp. 520-525.
Siles, Samuel A. et al.; "High-Throughput Screening of a Collection of Known Pharmacologically Active Small Compounds for Identification of Candida albicans Biofilm Inhibitors"; Antimicrobial Agents and Chemotherapy; vol. 57; No. 8; Aug. 2013; pp. 3681-3687.
Vandenbosch, Davy et al.; "Phytosphingosine-1-Phosphate Is a Signaling Molecule Involved in Miconazole Resistance in Sessile Candida albicans cells"; Antimicrobial Agents and Chemotherapy; vol. 56; No. 5; May 2012; pp. 2290-2294.
Vandeputte, Patrick et al.; "Antifungal Resistance and New Strategies to Control Fungal Infections"; International Journal of Microbiology; 2012; 2012; 27pp.
Wächtler, Betty et al.; "Candida albicans Adhesion to and Invasion and Damage of Vaginal Epithelial Cells: Stage-Specific Inhibition by Clotrimazole and Bifonazole"; Antimicrobial Agents and Chemotherapy; vol. 55; No. 9; Sep. 2011; pp. 4436-4439.
Wilson, Leslie S. et al.; "The Direct Cost and Incidence of Systemic Fungal Infections"; Value in Health; vol. 5; No. 1; 2002; pp. 26-34.

\* cited by examiner

Octodrine

Pyrithione Zinc

METHOD OF TREATING MICROBIAL INFECTIONS

FIELD

This disclosure is directed to methods of inhibiting or treating fungal and/or microbial growth in living organisms, in water, in air, and on surfaces.

BACKGROUND

Several clinical and laboratory data suggests that currently available antifungal therapies are mostly ineffective in treating *Candida* infections. Despite extensive research dedicated to the development of new therapeutic strategies, there are only a limited number of available drugs to fight against invasive fungal infections. Indeed, only four molecular classes targeting three distinct fungal metabolic pathways are currently used in clinical practice to treat systemic fungal infections. These include: fluoropyrimidine analogs, polyenes, azoles, and echinocandins. However, the efficacy of some of these drugs is severely limited because of unacceptable toxicity, poor activity in blood, and/or the emergence of resistance. Several other classes, such as morpholines and allylamines are only used as topical agents due to either their poor efficacy or severe adverse effects when administered systemically. These limitations underscore an urgent necessity for new antifungal agents. Furthermore, the development of an entirely new drug is a long and expensive process. New drugs have to undergo an arduous approval process by the Food and Drug Administration (FDA) in order to establish safety of the drug for human consumption.

SUMMARY

Some embodiments of the present invention are directed to methods of inhibiting the proliferation of a fungus and/or a bacteria in a living organism, the methods including administering to the living organism a therapeutic amount of an antimicrobial composition including Octodrine.

In some embodiments, a method of treating a fungal infection in a living organism includes administering to the living organism a therapeutic amount of an antimicrobial composition including Octodrine.

Some embodiments of the present invention are directed to methods of inhibiting and/or preventing the proliferation of bacteria and/or fungi in air, water, and/or surfaces, the methods including administering an effective amount of an antimicrobial composition comprising Octodrine to the air, water, and/or surfaces.

BRIEF DESCRIPTION OF THE DRAWINGS

The patent or application file contains at least one drawing executed in color. Copies of this patent or patent application publication with color drawings will be provided by the Office upon request and payment of the necessary fee.

These and other features and advantages of the present invention will be better understood by reference to the following detailed description when considered in conjunction with the accompanying drawings.

DETAILED DESCRIPTION

Figure 1A:
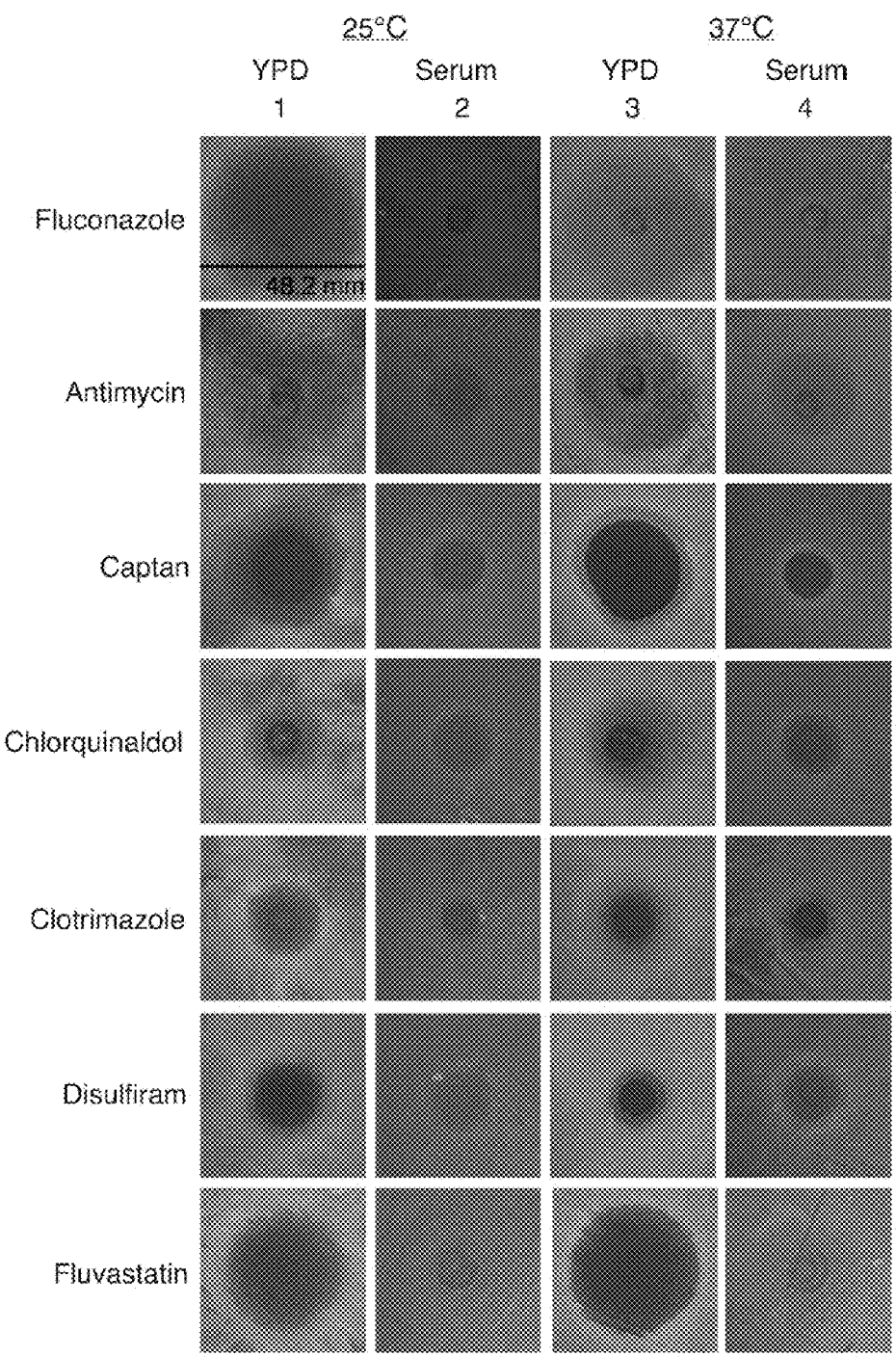
FIG. 1A shows photographs of YPD and serum plates each at 25° C. and 37° C., each of which plate was inoculated with a liquid culture of *Candida albicans* strain SN250 followed by the test compound, as indicated on left in the drawing, according to embodiments of the present invention.
Figure 1A:
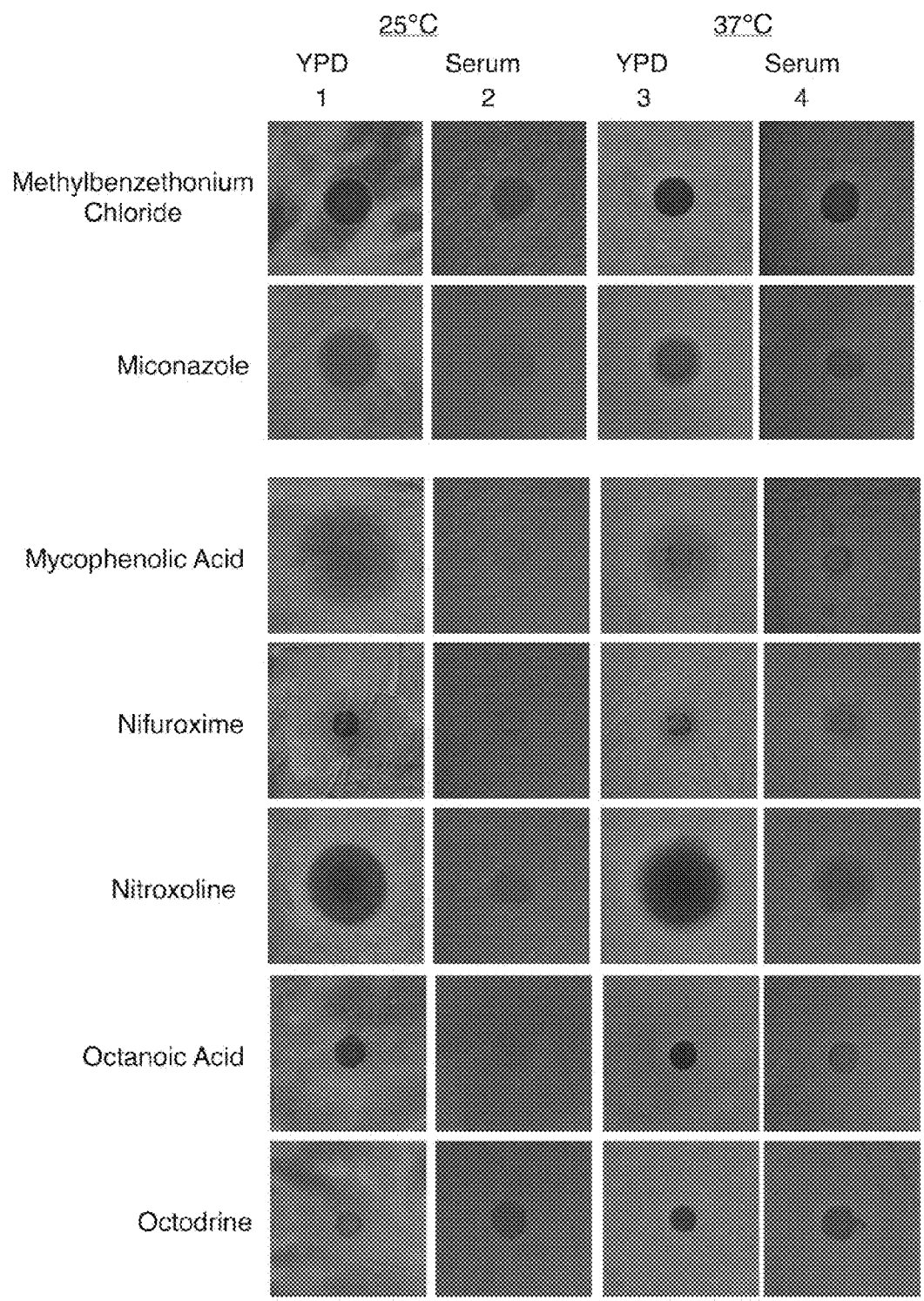
Figure 1A:
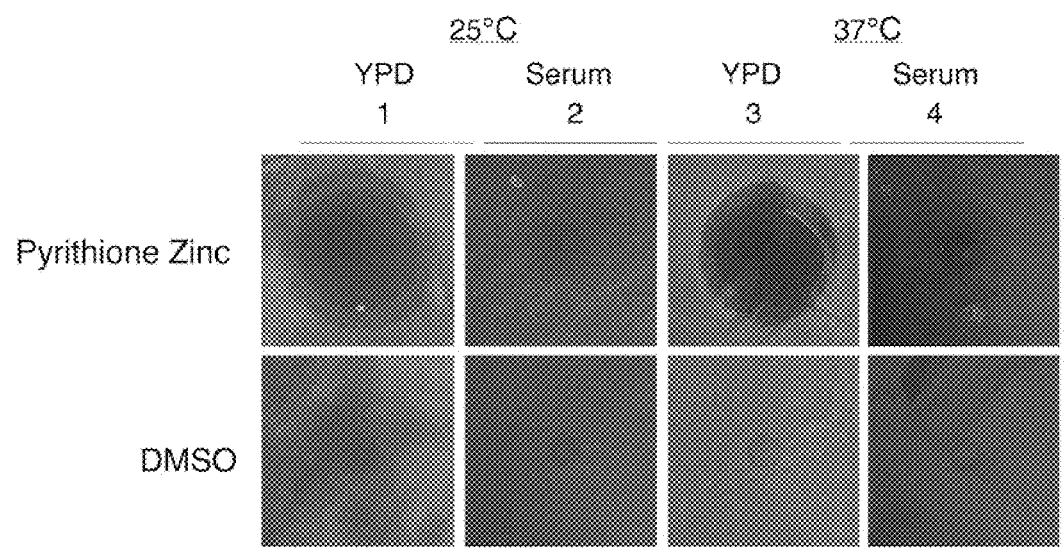

Embodiments of the present invention are directed to the use of 6-methylheptan-2-amine for inhibiting microbial growth. The compound 6-methylheptan-2-amine is also known and referred to as Octodrine. In some embodiments, administration of Octodrine inhibits the proliferation of microbial growth, including growth of fungi of the genus *Candida* and both gram-negative and gram-positive bacteria. In some embodiments, administration of Octodrine inhibits the proliferation of the fungus *Candida Albicans*. In some embodiments, a method of inhibiting growth of *Candida Albicans* includes administering a therapeutic amount of Octodrine alone, or a therapeutic amount of a composition including Octodrine to a living organism in need thereof. In some embodiments, a method of inhibiting growth of a gram negative bacteria or gram positive bacteria includes administering a therapeutic amount of Octodrine alone or a therapeutic amount of a composition including Octodrine to a living organism in need thereof.

The term "prevent" as used herein refers to all activities to inhibit the microbial infection or retard the pathogenesis of the microbial infection by administering the composition comprising Octodrine. That is, the term prevent includes the lack of antimicrobial growth in a living organism, water, air, or on a surface that has been exposed to a microbe such as fungi and/or gram negative or gram positive bacteria.

As used herein, the term "treat" refers to all activities to improve or favorably change the symptoms of the microbial (e.g., fungal) infection by administering the composition comprising Octodrine.

As used herein, the term "therapeutic amount" or "effective amount" refers to the amount of the composition including Octodrine that attains the desired effect, such as the inhibition of, the progression of, or the onset of the particular microbial growth being treated. The microbial growth to be treated may be on any surface or may be an infection within a living organism. A therapeutic amount or an effective amount may range from about 10 mM to neat. The density of Octodrine is reported as 0.767 g/ml.

As used herein, the term "living organism" refers to any living organism that is capable of contracting a microbial infection, including a fungal infection and other microbial infections. A living organism having a microbial infection is in need of an anti-microbial, such as Octodrine. Non-limiting examples of a living organism include all mammals, birds, fish, and plants, as well as the cells from these living organisms. An example of a mammal is a human.

Microbial infections, including fungal and bacterial infections may include, for example, systemic candidiasis, oral *candida* thrush, urinary tract infections, *Candida* skin infections, yeast vaginal infections, bacterial systemic infections, bacterial skin infections, and bacterial gastrointestinal infections.

As used herein, the terms "composition" or "pharmaceutical composition" are used interchangeably and refer to compositions or formulations that in addition to the active ingredient (e.g., Octodrine), may also include an excipient, such as a pharmaceutically acceptable carrier, that are conventional in the art and that are suitable for administration to living organisms, including mammals (e.g., humans), and cells thereof. Such compositions can be specifically formulated for administration via one or more of a number of routes, including but not limited to, oral, parenteral, intravenous, intraarterial, subcutaneous, intranasal, sublingual, intraspinal, intracerebroventricular, or the like. Cells may be administered with the Octodrine composition as disclosed herein for example, for therapeutic, diagnostic, or prophylactic purposes. These cells may be part of a subject, e.g., living organism. The cells may also be cultured, for example, cells that are a part of an assay for screening potential pharmaceutical compositions; and the cells may be a part of a transgenic animal for research purposes. In addition, compositions for topical (e.g., oral mucosa, respiratory mucosa) and/or oral administration may form solutions, suspensions, tablets, pills, capsules, sustained-release formulations, oral rinses, or powders, as known in the art.

In addition to excipients, the compositions according to disclosed embodiments may also include stabilizers, preservatives, and/or adjuvants. Drug stabilizers and preservatives are used to increase the shelf life of the composition. Adjuvants are used with a drug to increase the immunogenic response to the drug. Examples of carriers, stabilizers and adjuvants are disclosed in Hamill, R J, *Drugs,* 2013, 73:919-934 (PMID 23729001), the entire contents of which are incorporated by reference.

Octodrine compositions as disclosed herein may be administered by any convenient route, including parenteral, enteral, mucosal, topical, e.g., subcutaneous, intravenous, topical, intramuscular, intraperitoneal, transdermal, rectal, vaginal, intranasal or intraocular. In one embodiment, the delivery is by oral administration of the composition formulation. In one embodiment, the delivery is by intranasal administration of the composition. Along these lines, intraocular administration is also possible. In another embodiment, the delivery means is by intravenous (i.v.) administration of the composition, which is especially advantageous when a longer-lasting i.v. formulation is desired. Suitable formulations can be found in PMID 23729001, supra.

The Octodrine compositions, as disclosed herein, may be administered in prophylactically or therapeutically effective amounts. The Octodrine composition herein may be administered along with a pharmaceutically acceptable material—such as an excipient, carrier, stabilizer, and/or adjuvant. A prophylactically or therapeutically effective amount means the amount necessary, at least partly, to attain the desired effect, or to delay the onset of, inhibit the progression of, or halt altogether the onset or progression of the particular microbial infection being treated. Such amounts will depend on the particular condition being treated, the severity of the condition and individual patient parameters including age, physical condition, size, weight and concurrent treatment. These factors are well known to those of ordinary skill in the art and can be addressed with no more than routine experimentation. If possible a maximum dose should be administered. The maximum dose is the highest safe dose according to sound medical judgment. It will be understood by those of ordinary skill in the art, however, that a lower dose or tolerable dose may be administered for medical reasons, psychological reasons or for any other reason.

As used herein, the term "pharmaceutically acceptable material" refers to any pharmaceutically acceptable means to mix and/or deliver the Octodrine composition to a living organism. Examples of pharmaceutically acceptable materials include liquids, solid fillers, diluents, excipients, solvents and/or encapsulating materials, involved in sustaining, carrying and/or transporting the subject agents (e.g., the Octodrine) from one organ, or portion of the body, to another organ, or portion of the body. The carrier material must be "acceptable" in the sense of being compatible with the other ingredients of the formulation and is compatible with administration to the particular living organism, for example a human or the cells of a human. For the clinical use of the methods of the present invention, the Octodrine composition of the invention is formulated into pharmaceutical compositions or pharmaceutical formulations for parenteral administration, e.g., intravenous; mucosal, e.g., intranasal; enteral, e.g., oral; topical, e.g., transdermal; ocular, e.g., via corneal scarification or other mode of administration. The pharmaceutical composition contains a compound of the invention in combination with one or more pharmaceutically acceptable materials, for example, a carrier. The carrier may be in the form of a solid, semi-solid or liquid diluent, cream or a capsule. The amount of Octodrine in the pharmaceutical composition according to embodiments of the present invention may be between 0.1-95% by weight of the preparation, for example, between 0.2-20% by weight in preparations for parenteral use, and between 1 and 50% by weight in preparations for oral administration.

As used herein, the term "parenteral administration" and "administered parenterally" means modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. The phrases "systemic administration," "administered systemically," "peripheral administration" and "administered peripherally" as used herein mean the administration of a compound, drug or other material other than directly at a site of infection, such that it enters a system of the living organism (e.g., the circulatory system, the respiratory system, or through the skin) and, thus, is subject to metabolism and other like processes.

As used herein, the terms "administering" and "introducing" are used interchangeably and refer to the placement of the pharmaceutical composition including an Octodrine composition according to some embodiments of the present invention, into a living organism or cells thereof by a method or route which results in at least partial localization of the Octodrine at a desired site. The antimicrobial Octodrine composition according to embodiments of the present invention may be administered by any appropriate route which results in an effective treatment in the living organism in need thereof.

In the preparation of pharmaceutical doses of the Octodrine composition for oral administration, the Octodrine composition may be mixed with solid, powdered ingredients, such as lactose, saccharose, sorbitol, mannitol, starch, amylopectin, cellulose derivatives, gelatin, and/or another suitable ingredient, as well as with disintegrating agents and lubricating agents such as magnesium stearate, calcium stearate, sodium stearyl fumarate and/or polyethylene glycol waxes. The mixture may then be processed into granules or pressed into tablets.

In some embodiments, the Octodrine composition includes an additive. An additive may include any addition component that enhances the antimicrobial effectiveness of the Octodrine. Non-limiting examples of additives include other antifungals, antibacterials, antibiotics, antimicrobials, antivirals, antiparasitics, or combinations thereof, as disclosed in Brambilla, G. et al., *Mutagenesis,* 2012, 27:387-413, (PMID: 22228823), the entire content of which is incorporated herein by reference.

In some embodiments, the Octodrine composition may be used to eliminate, prevent, or inhibit the proliferation of microbes in water, air, and/or on surfaces. As such, the Octodrine composition may be used as an antifungal and/or antibacterial disinfectant in water. For example the Octodrine composition may be added to water to prevent antifungal and/or antibacterial growth in the water to be consumed by, or given to a living organism. In some embodiments, a disinfectant composition of the present invention includes an effective amount of Octodrine. The Octodrine composition for use as a disinfectant may be in any acceptable form. An acceptable form of Octodrine is any form of Octodrine that provides the antimicrobial (e.g. antifungal) effects of Octrodrine. An acceptable form may include Octodrine and an acceptable carrier. An acceptable carrier as described herein includes all the suitable carriers and components as described for a pharmaceutically acceptable material that enhance the use of the Octodrine as a disinfectant. In some embodiments, the disinfectant composition of the present invention also includes one or more of the following: a surfactant, water, and an aliphatic alcohol. In some embodiments, the surfactant may be ionic or nonionic. In some embodiments, the disinfectant composition may include both an ionic surfactant and nonionic surfactant. In some embodiments, the disinfectant composition includes an alkaline agent and/or a chelating agent. Uses of an antimicrobial in water, air, and/or on surfaces are disclosed in PMID 23729001, supra.

In some embodiments, the Octodrine composition may be used in the processing, preparation, handling, and/or packaging of any food for consumption by a living organism, for example, food to be consumed by livestock, domestic animals, and/or humans. That is, as described for a surface herein, the surface of the food and/or the food packaging may be treated with the composition having an effective amount of Octodrine. The Octodrine composition may be applied to the food or the food packaging to prevent microbial growth on or within the food. As such, food that can serve as sustenance for a microbe may be protected from microbial growth with an application of the Octodrine composition as disclosed herein. The Octodrine composition may be administered to the food or the food packaging in any acceptable form. An acceptable form of Octodrine may include a neat form of Octodrine. An acceptable form may include Octodrine in a diluted concentration. In some embodiments, the amount of Octodrine in the applied acceptable form may be from about 10 mM up to the neat form.

In some embodiments, the Octodrine composition of the present invention may be used to decontaminate or prevent the contamination of drinking water by microbes.

In an effort to find an FDA-approved drug for use as an antimicrobial/anti-fungal agent, drugs previously approved by the FDA for a non-microbial purpose were screened. Specifically, FDA-approved drugs from the Johns Hopkins Clinical Compound Library (JHCCL) (Chong et al., 2006, Nat. Chem. Biol. 2:415-416, the entire contents of which are incorporated herein by reference) were screened for anti-*Candida* activity. This JHCCL library consists of drug-compounds that are FDA-approved with a diverse range of functions, mechanisms of action and well-characterized pharmacological and toxicological properties.

The following Examples are presented for illustrative purposes only, and do not limit the scope or content of the present application.

EXAMPLES

Example 1

Inability of fluconazole to kill serum-grown *Candida albicans* at 37° C.

It has been reported that host serum markedly inhibits growth of the human fungal pathogen, *Candida albicans* (Hendry et al., 1969, *Sabouraudia* 7:219-229; Elin et al., 1973, *J. Infect. Dis.* 127:705-708; King et al., 1975, *J. Lab Clin Med,* 86:204-212, the entire contents of all of which are herein incorporated by reference.) It was confirmed that *Candida* wild type strain SN250 (described in Noble S M et al., 2010, *Nat Genet* 42: 590-598, the entire content of which is incorporated herein by reference), is unable to grow in liquid 100% Fetal Bovine Serum (FBS) at either 25° C. or 37° C. However, as shown in FIG. 1A, *Candida* is able to grow and establish a lawn on solid serum plates containing FBS and agar, at both 25° C. and 37° C.

As shown in FIG. 1A, the widely used anti-*candida* drug fluconazole was able to kill *C. albicans* on solid serum plates. However, while fluconazole was shown to be an effective inhibitor of *Candida* growth on solid YPD plates, fluconazole poorly inhibits the growth of *Candida* on serum plates (FIG. 1A). Fluconazole formed prominent halos on the solid YPD plates. In addition, fluconazole exhibited diminished effectiveness at forming halos at 37° C. compared to 25° C.

Example 2

Screening of inhibitors of *Candida albicans* lawn formation

In light of the ineffectiveness of fluconazole to kill *C. albicans* in serum at the physiologically relevant temperature (37° C.), and in search for alternative anti-fungal drugs, the library of chemicals (Chong et al., 2006, supra), approved by the FDA for human use was screened for ability to kill *Candida albicans*. The JHCCL library consists of 1,581 FDA-approved compounds consisting of small molecules (10 mM) that are used as treatments for a variety of diseases, including, but not limited to: infectious, neurodegenerative, psychiatric, cardiovascular diseases and cancer.

Figure 1B:
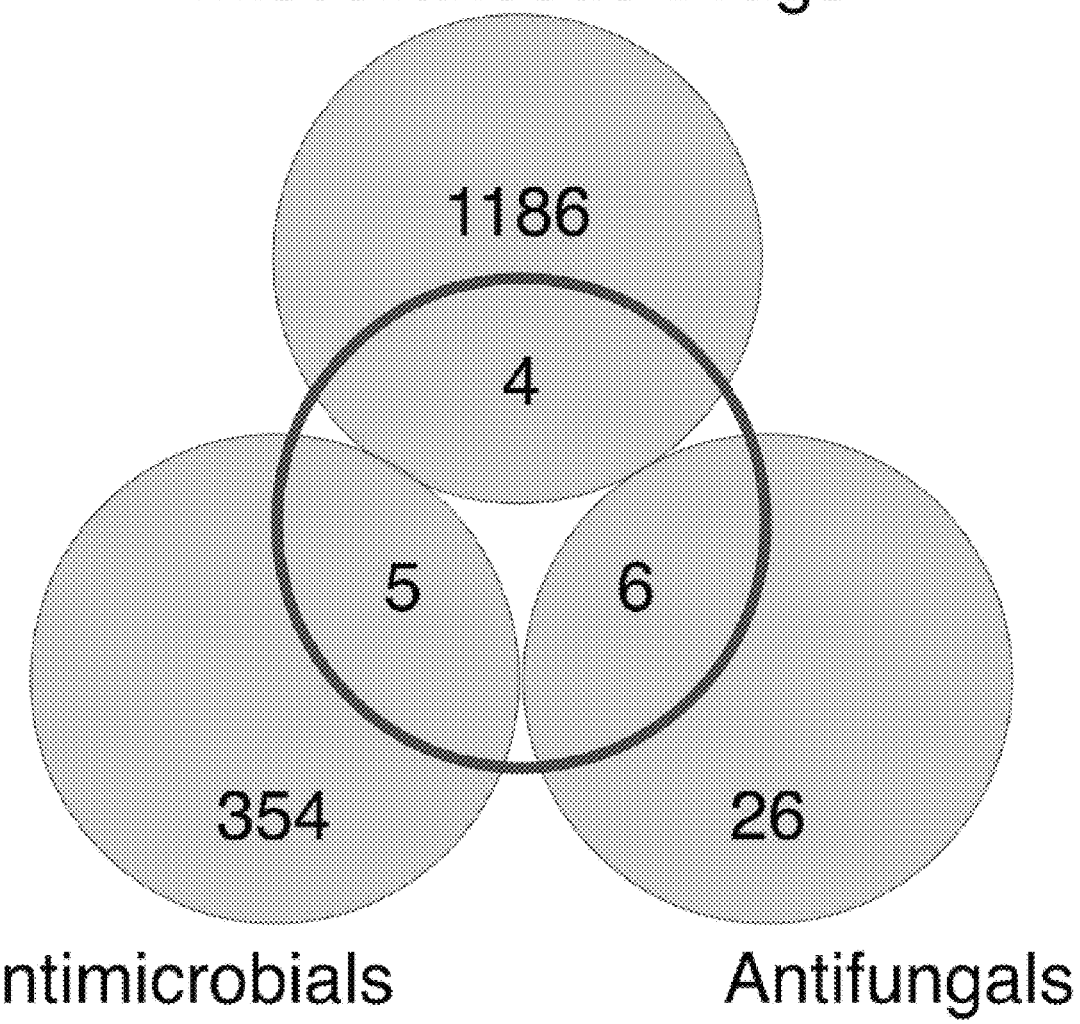
FIG. 1B is a schematic showing the classification (e.g., antimicrobial, antifungal, or miscellaneous) of the 15 drugs that were "hits" against the *Candida albicans* in FIG. 1A, according to embodiments of the present invention.
Figure 2A:
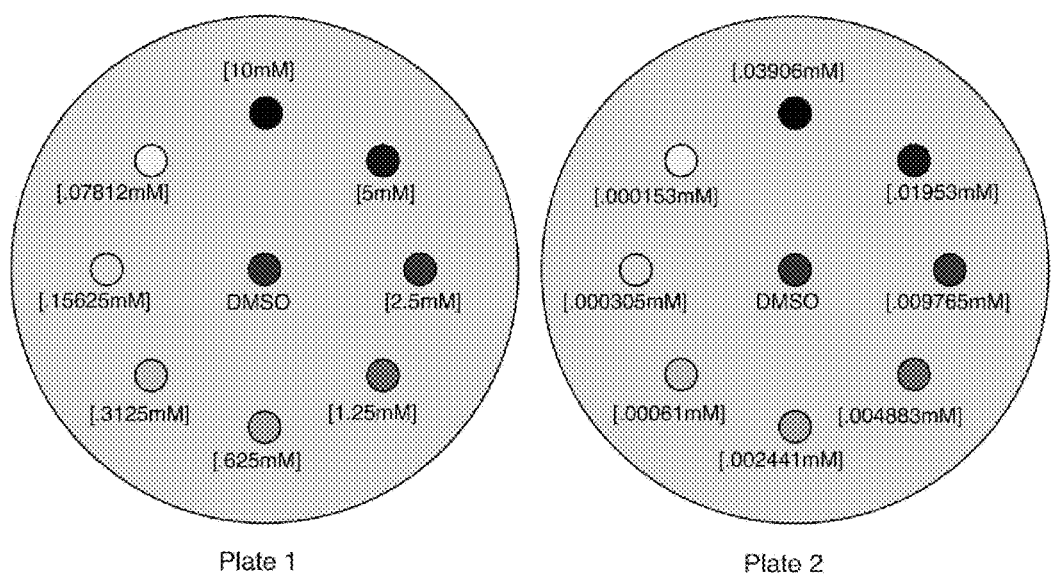
FIG. 2A shows the concentration of the compounds of interest on Plate 1 and Plate 2 in the serial dilution experiment shown in FIG. 2B, according to embodiments of the present invention.
Figure 2B:
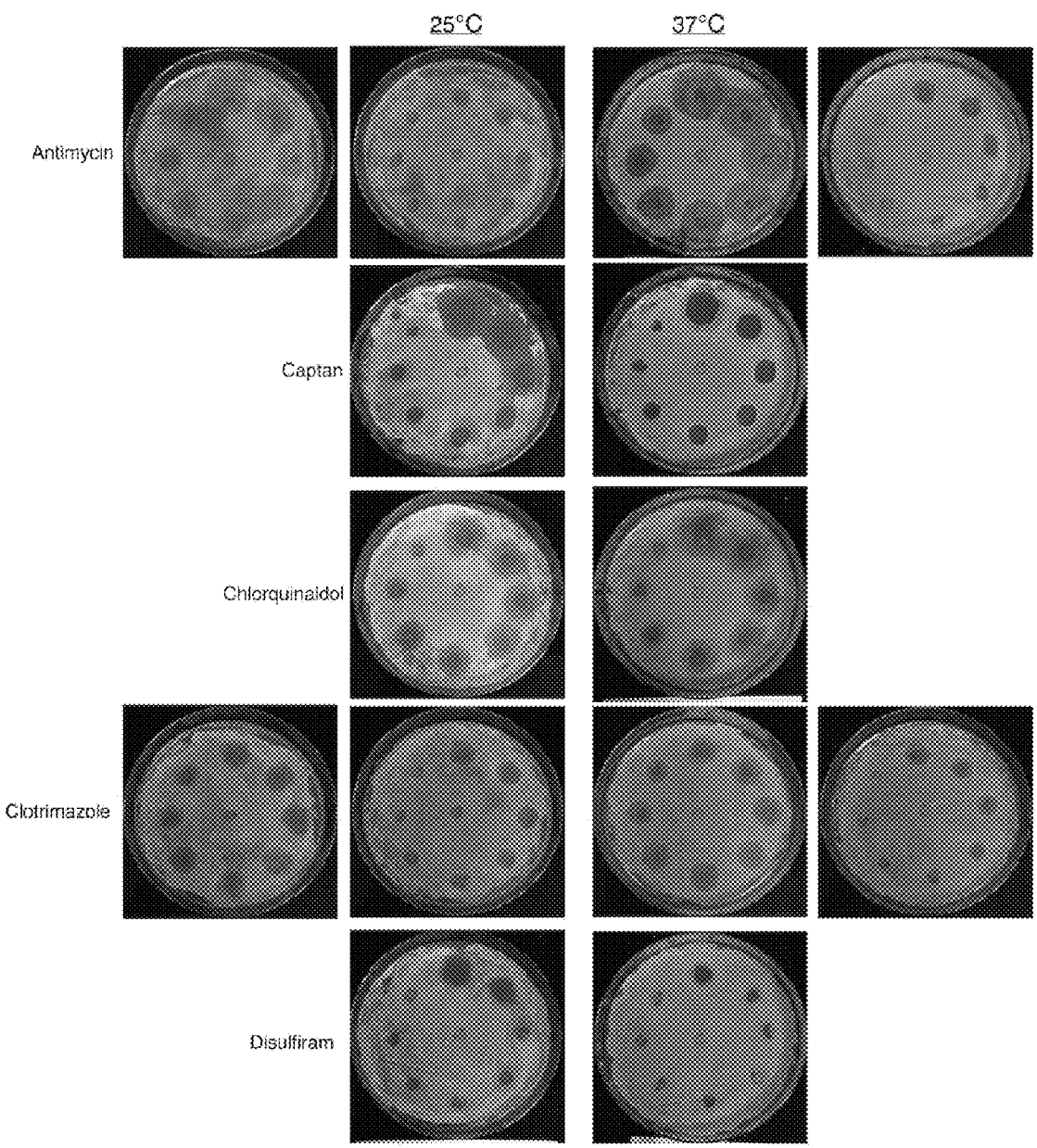
FIG. 2B shows the results for the dose-determinant response against *Candida albicans* SN250 for the compounds of interest as indicated to the left of each row, at 25° C. and 37° C.; a subsequent dilution was added at each temperature for antimycin, clotrimazole, miconazole, and octanoic acid, as shown, according to embodiments of the present invention.
Figure 2B:
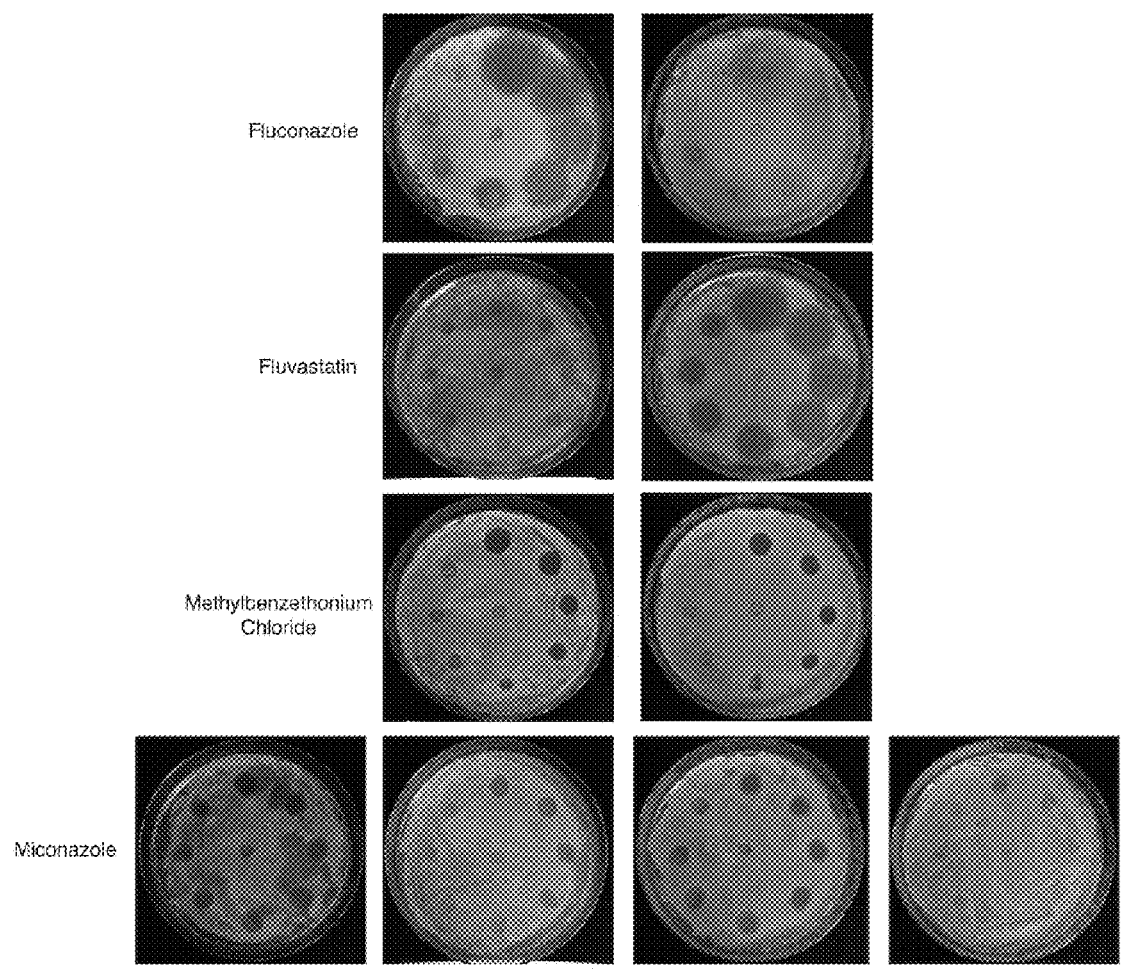
Figure 2B:
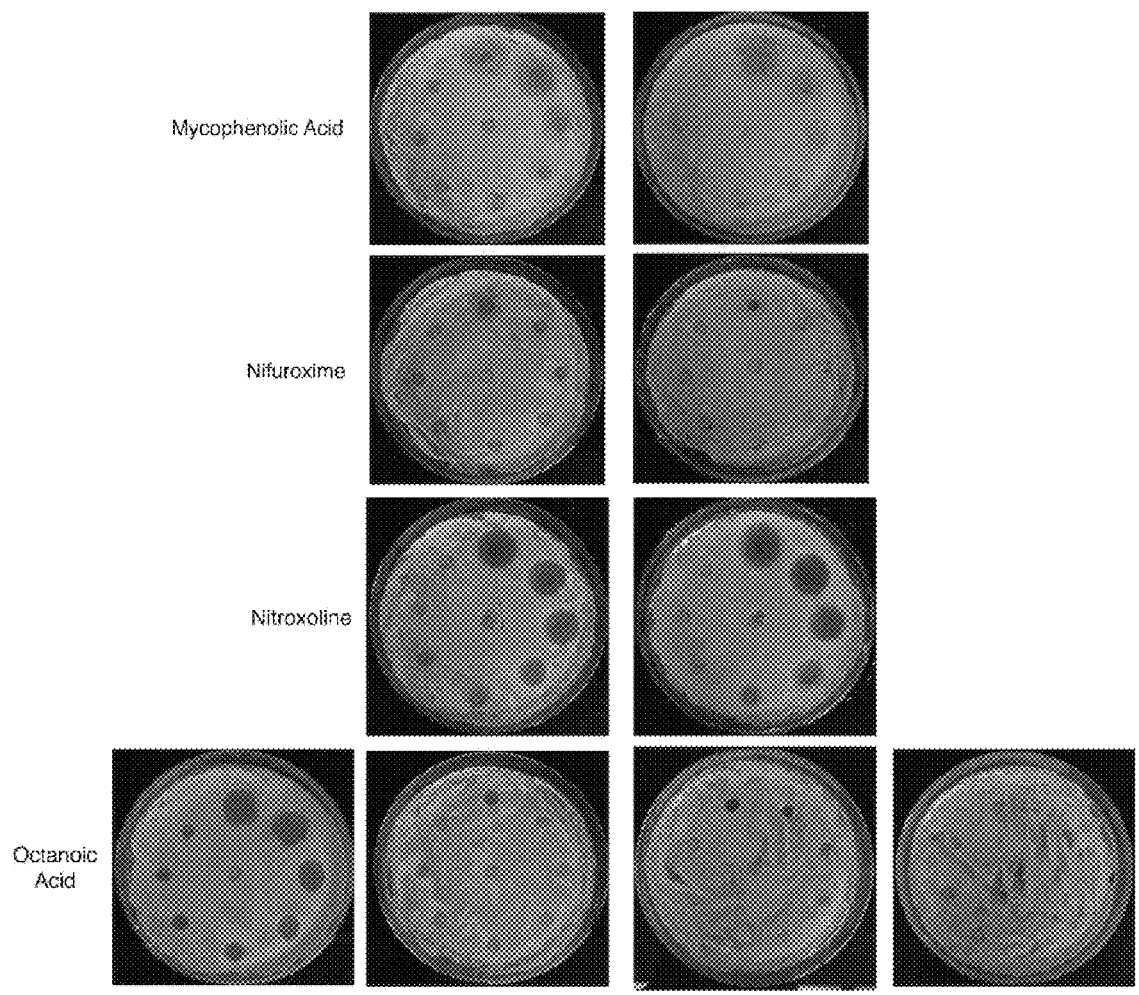
Figure 2B:
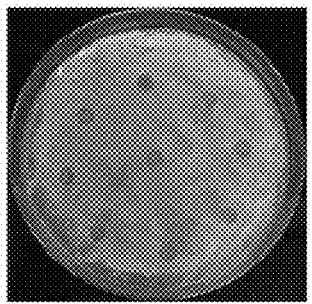
Figure 2B:
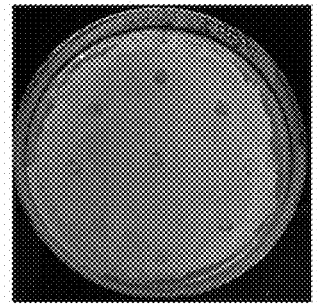
Figure 2B:
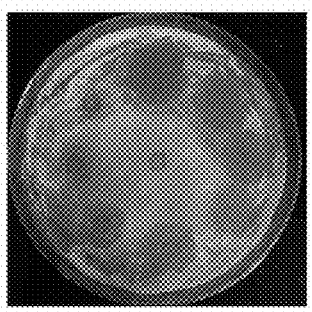
Figure 2B:
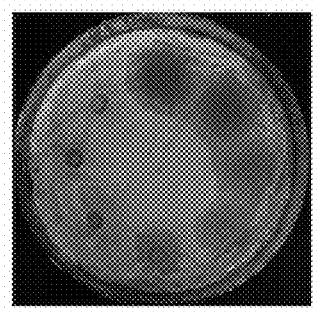

Inhibitors of *C. albicans* growth formation were identified by performing a primary screen on the 1,581 compounds of the JHCCL library. *C. albicans* was plated on solid YPD and serum plates, and 5 µl of each 10 mM drug was placed on top of the fungal lawn. The effect of exposure to each of the compounds from the library was assayed for its ability to inhibit *C. albicans* growth, as well as ability to form a halo within the fungal lawn. Based on this screen, 15 compounds were identified that inhibit *C. albicans* growth on YPD alone or on both YPD and serum plates in at least five independent experiments at two temperatures of 25° C. and 37° C. (FIG. 1A). The 15 hits were classified into three different classes for interpretation. The classes included: 5 hits from 31 known antifungals, 6 hits from 360 antimicrobials/antiseptics, and 4 hits from 1190 other multifunctional drugs (FIG. 1B). While these compounds were chosen in these screens for their ability to inhibit *C. albicans* lawn formation, the actual levels of inhibition varied from weak to strong inhibition (FIG. 1A).

All 6 selected antifungal drugs, Antimycin A, Captan, Clotrimazole, Fluconazole, Miconazole, and Pyrithione Zinc, showed strong inhibition of *C. albicans* growth on YPD plates at 25° C. and 37° C. (FIG. 1A). However, with the exception of the pesticide Captan, all of the antifungals exhibited weak inhibition of *C. albicans* growth on serum plates as shown.

Out of the 5 antimicrobial/antiseptic drugs selected by the screen, Chlorquinaldol and Methyl-benzethonium chloride displayed the strongest inhibition of *C. albicans* growth on serum plates. Nifuroxime, Nitroxoline, and Octanoic acid showed weaker inhibition of *C. albicans* growth on serum plates Interestingly, 4 drugs from the 1190 of the other multifunctional drugs, showed anti-*C. albicans* activity on YPD plates (FIG. 1A). Of those 4, Fluvastatin and Mycophenolic acid showed very strong inhibition of YPD-grown *Candida*, but failed to inhibit its growth on serum plates (FIG. 1A). Surprisingly, the other 2 drugs, Disulfiram and Octodrine showed a moderate-to-weak anti-*Candida* activity on YPD, but a strong fungal growth inhibition on serum plates (FIG. 1A).

Example 3

Dose-response Assays of the Hits obtained from the Screen

The 15 hits from the primary screen consisting of antifungals, antimicrobials, and miscellaneous drugs were tested in dose-response assays in order to determine their potency against *C. albicans* lawns. These confirmatory screenings were performed over a range of drug concentrations, where 5 µl of drugs within the range of 10 mM to 0.3 µM were applied on YPD-grown *C. albicans* cells and plates were incubated for 24 hours. The efficacy of each drug was evaluated by estimating the inhibitory concentration at which the drug formed a halo on a fungal lawn of YPD plates.

With the exception of fluconazole and captan, all antifungals were able to inhibit *Candida* growth in the µM drug range (FIG. 2), whereas all five antimicrobial and antiseptic drugs were only able to inhibit fungal growth in the mM drug concentrations (FIG. 2). Surprisingly, among the drugs approved for non-infectious disease treatments, fluvastatin was able to inhibit *C. albicans* growth in the µM drug concentration, while the remaining drugs were only inhibitory in the mM drug concentrations.

Example 4

Broad-Spectrum Antimicrobial Properties of Octodrine

The 9 identified antimicrobial and non-antimicrobial drugs have not been approved by FDA to treat fungal infections, however, eight of them were previously reported to kill *C. albicans*. See, for example, Kot, E J et al. 1976, *Antonie Van Leeuwenhoek* 42: 33-48; Gale, G R et al., 1971, *Toxicol Appl Pharmacol* 18: 426-441; Lovgren, T et al., 1978, *Acta Pathol Microbiol Scand* B 86B: 155-158; Wachtler, B et al., 2011, *Antimicrob Agents Chemother* 55: 4436-4439; Shukla, S et al., 2004, *Biochem Biophys Res Commun* 322: 520-525; Molepo, J et al., 2012, SADJ 67:326-328; Nash J D et al., 2002, *J Med Microbiol* 51:105-109; Ichikawa, T et al., 2008, *J Dent* 36: 965-968; Vandenbosch, D et al., 2012, *Antimicrob Agents Chemother* 56: 2290-2294; Kohler, G A et al., 2005, *J Biol Chem* 280: 11295-11302; Grossman, L I et al., 1967, *J Dent Res* 46: 215-217; Hernandez Molina, J M et al., 1991, *Mycoses*, 34:323-325; Omura, Y et al., 2011, *Acupunct Electrother Res* 36:19-64; and De Prijck, K et al., 2010, *Mycopathologia*, 169:167-174, the entire contents of all of which are herein incorporated by reference.

Notably, a 5 µl drop of 10 mM Octodrine showed a prominent ability to kill serum-grown *C. albicans*. Octodrine is a drug previously used as a decongestant. Furthermore, Octodrine is the only drug that has not previously been tested to kill fungi. In order to investigate whether the application of an even higher concentration of Octodrine would augment its antifungal properties, 5 µl of undiluted Octodrine (approximately 3 mg; density of Octodrine is reported as 0.767 g/ml) was placed in the middle of a serum grown *Candida* lawn. This amount of Octodrine was sufficient to eliminate most of the whole fungal lawn.

Figure 3:
FIG. 3 shows the effect of Octodrine on *Candida albicans* knock-out mutants on YPD plates exposed to 5 μl of 10 mM Octodrine, according to embodiments of the present invention. A representative part of the plated mutants is shown along with the wild type strain, as detailed herein, according to embodiments of the present invention.

In order to identify *C. albicans* proteins and signaling pathways that mediate the lethality of Octodrine, three *C. albicans* knockout libraries were screened for any alterations in sensitivity to 10 mM Octodrine—collectively consisting of 908 mutant strains each strain lacking one of the virulence genes. These libraries consisted of 647 mutant strains lacking one of the essential virulence genes (Noble, S M et al., 2010, *Nat Genet* 42:590-598, the entire content of which is herein incorporated by reference); 96 cell wall protein mutants (Norice, C T et al., 2007, *Eukaryot Cell* 6:2046-2055, the entire content of which is herein incorporated by reference); and 165 transcription factors mutants (Nobile, C J et al., 2005, *Curr Biol* 15:1150-1155, the entire content of which is herein incorporated by reference). All of the *C. albicans* mutants were as sensitive as their wild type strains. FIG. 3 shows a representation of all of the *C. albicans* mutants. FIG. 3 shows the sensitivity from the following mutants: ORF19.113, ORF19.118, ORF19.260, ORF19.278, ORF19.287, ORF19.376, ORF19.380, ORF19.936, ORF19.993, ORF19.1002, ORF19.1049, ORF19.1162, ORF19.1171, ORF19.1239, ORF19.1625, ORF19.1634, ORF19.1710, ORF19.1797, ORF19.1860, ORF19.2108, ORF19.2133, ORF19.2284, ORF19.2429, ORF19.2461, ORF19.2463, ORF19.2500, and ORF19.2570, as well as wild type.

Figure 4:
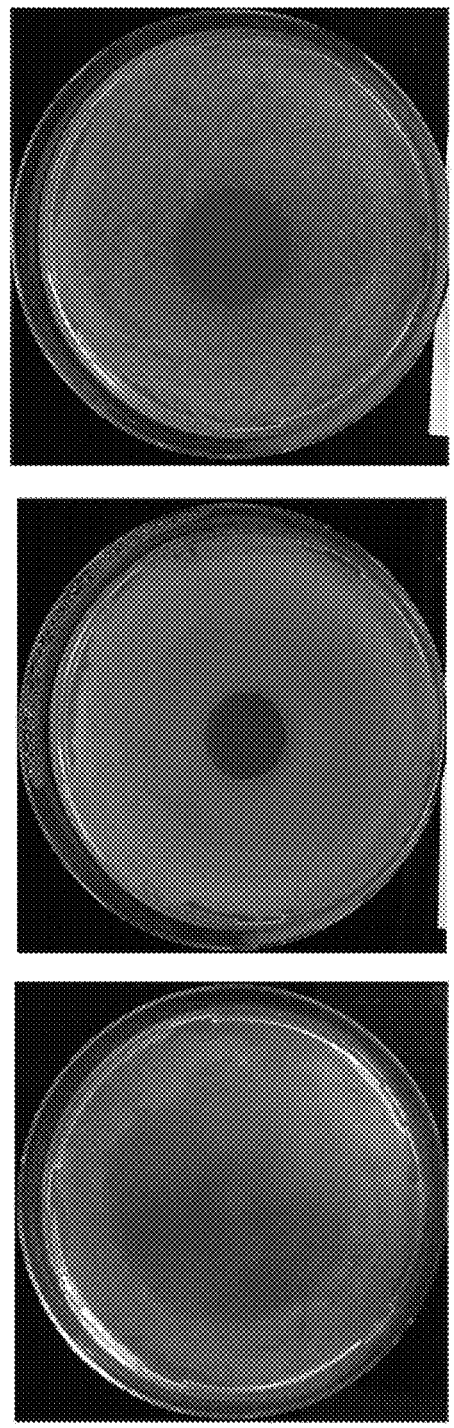
FIG. 4 shows the effect of Octodrine in neat form against the growth of *Candida albicans, Bacillus cereus*, and *Escherichia coli* as indicated, according to embodiments of the present invention.

In order to test if Octodrine kills microorganisms by targeting their non-protein cellular components, *Escherichia coli* and *Bacillus cereus*, gram-negative and gram-positive bacteria respectively, were exposed to Octodrine. As shown in FIG. 4, 5 µl of Octodrine in the neat form (3 mg of undiluted) formed prominent halos in both *E. coli* and *B. cereus* lawns, indicating that Octodrine possesses wide spectrum antimicrobial properties.

Figure 5:
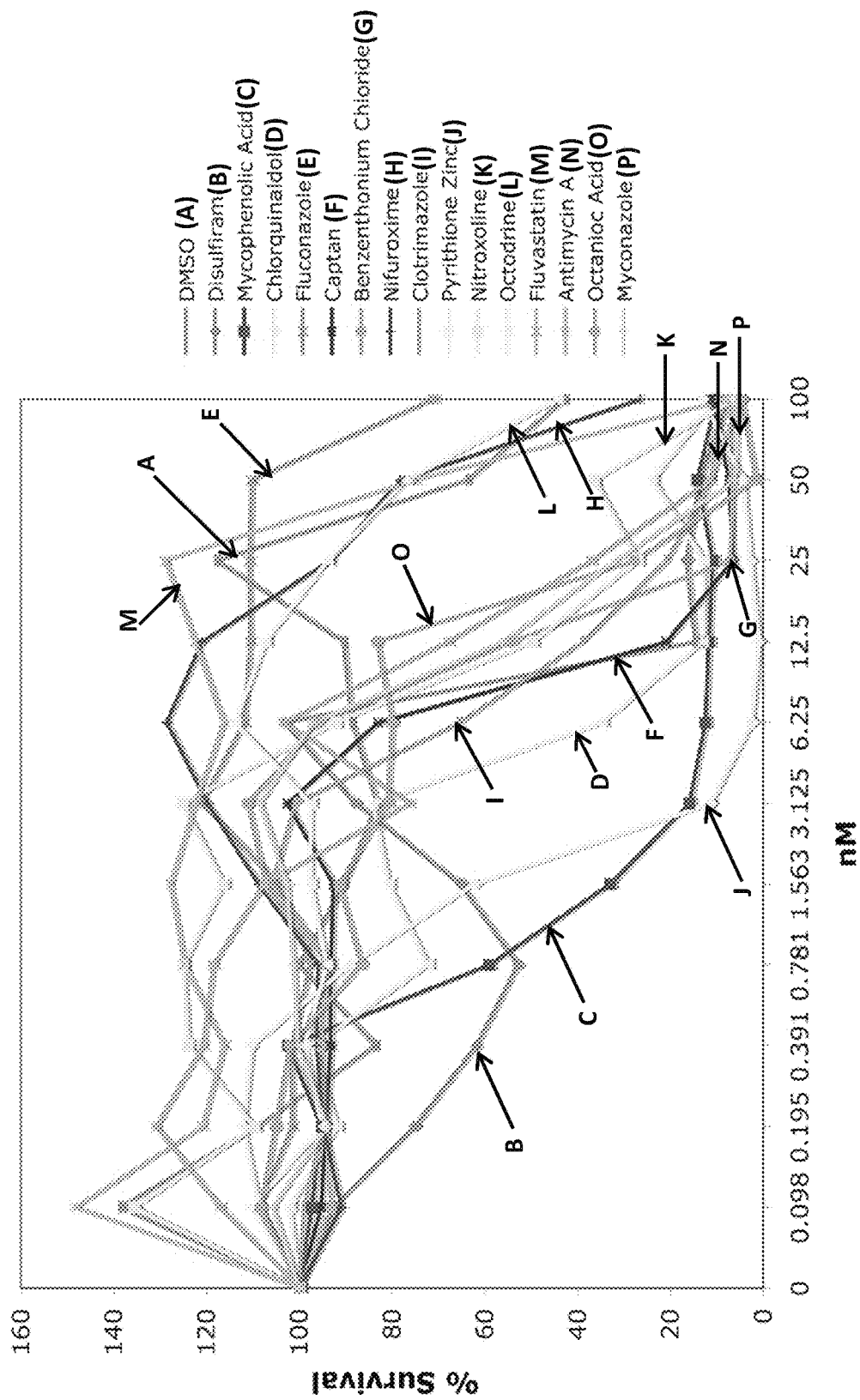
FIG. 5 is a graph of the percent cell survival (Y-axis) relative to untreated cells (X-axis) for various drugs, according to embodiments of the present invention.

Since Octodrine was the most prominent drug that killed *C. albicans* in serum, the sensitivity of mouse macrophage cell line RAW264.7 to Octodrine was tested, and compared to the rest of the selected drugs as indicated in FIG. 5. The sensitivity of mouse macrophages to Octodrine was the same as to the DMSO alone, thereby indicating that Octodrine concentrations that kill *Candida albicans* in serum do not affect the survival of host phagocytes. With the exception of floconazole, all other selected drugs adversely affected the survival of host cells, which suggests that they may have undesirable side effects when used in blood. Although fluconazole did not affect the survival of mouse macrophages, it was shown to be ineffective in killing *C. albicans* in serum (FIG. 1A).

Materials and Methods Used

*Candida albicans* and Bacterial Strains: The *Candida albicans* wild type strain SN250 was used for the high-throughput screening experiments. The bacterial strain consisted of *Bacillus cereus* strain 10987 and *Escherichia coli* strain C600. The genotypic screen for mutant sensitivity to Octodrine was tested with three *C. albicans* libraries that were previously created as disclosed in Noble, 2010, supra; Rauceo, J M et al., 2008, *Mol Biol Cell* 19:2741-2751; and Homann, O R et al., 2009, *PLoS Genet* 5:e1000783, the entire contents of all of which are herein incorporated by reference.

Media and Growth Conditions: *C. albicans* strains were cultured with 5 ml of YPD (1% yeast extract, 2% peptone, 2% dextrose, pH 6) medium at 30° C. overnight. Bacterial cells were cultured in LB (Luria-Bertani) medium consisting of 5 g Bacto-Tryptone, 2.5 g Bacto-Yeast Extract, 5 g NaCl and 7.5 g of 2% agar if preparing solid plates. The centrifuge tubes were incubated at 37° C. and left shaking overnight at 150 rpm. Fetal bovine serum was incorporated into agar. Fetal bovine serum was preheated in a water bath set at 65° C. The isothermal conditions of the two mixtures eliminated the formation of foam upon coalescence. The agar solution for the serum mixture consisted of 16 g agar, which was then brought up to 300 ml with nanopure water. The agar solution was then autoclaved at 120° C. for 45 minutes. The agar and serum mixtures were then amalgamated while in their isothermal states.

Chemicals: An FDA-approved drug library of 1500 drugs was purchased from Johns Hopkins, titled, Johns Hopkins Clinical Compound Library (JHCCL) version 1.0. The drugs arrived as 10 mM stock solutions in sealed microtiter plates and were made using DMSO or water as solvents. Drugs were arrayed in 96-well plates and screened at a stock concentration of 10 mM. The library was stored at −20° C. until use. Prior to use, the library of drugs was thawed at 25° C. Compounds that were determined to be compounds of interest were isolated and reproduced from prepared 10 mM solutions. Antimycin A, Captan, Chlorquinaldol, Clotrimazole, Disulfiram, Fluvastatin, Mycophenolic Acid, Methylbenzethonium Chloride, Miconazole, Nitroxoline, Octodrine, Pyrithione Zinc, Fluconazole, and Octanoic Acid were purchased from Sigma-Aldrich (St. Louis, Mo., USA). Nifuroxime was purchased from MP Biochemicals (Solon, Ohio, USA). All drugs were prepared to 10 mM using DMSO (dimethyl sulfoxide) as the solvent. DMSO was purchased from Amresco® (Solon, Ohio, USA). Fetal bovine serum (Triple Membrane 0.1 µm filtered) was purchased from GeneMate BioExpress (Kaysville, Utah, USA).

High-throughput Screening Assay: The sensitivity of *C. albicans* against compounds was assessed by a high-throughput chemical screen. 200 µl of *C. albicans* overnight culture were spread onto petri dishes containing either YPD or fetal bovine serum. 5 µl of each drug was placed directly on the agar surface using a multichannel pipette and slight contact of the tip to the agar made to leave an impression to facilitate later analysis. Compounds that were replicated were done on petri dishes, following the same protocol in at least five independent experiments. For the replication studies, only a single drug was placed per plate. The plates were incubated at either 25° C. or 37° C. The compounds-of-interest were selected on their ability to produce a distinct zone of inhibition of fungal growth greater than the zone made by DMSO alone and at the same time that is comparable to, if not greater than the positive control, Fluconazole.

Determination of minimal effective drug concentrations: Plates inoculated with *C. albicans* were prepared using the protocol described above. To elucidate the effect of differing concentrations on the ability of the drugs to form a halo, two-fold serial drug dilution experiments were performed. To perform the first two-fold dilution, one part of the 10 mM stock solution was mixed with one part DMSO. Each subsequent dilution was done with aliquots from the prior dilution mixed with equal parts of DMSO. 5 µl of each drug dilution was spotted onto a lawn grown on YPD plate, as well as 5 µl of DMSO as a negative control. Dilutions beyond 0.07813 mM that were still forming a significant halo were further diluted on a separate plate. Drug-treated plates were then incubated at either 25° C. or 37° C.

Genotypic Mutant Screening Against Octodrine: Each *C. albicans* knockout strain was cultured in individual wells of a 96 well plate in 100 µl of YPD media overnight at 30° C. 5 µl of each *Candida* knock-out overnight culture was spotted onto a YPD solid plate using a multichannel pipette. The cells were then left to absorb into the YPD plates for 1 hour at 25° C. Using a multichannel pipette, 5 µl of Octodrine 10 mM was spotted directly on top of the *C. albicans* cells. The plates were then placed in an incubator set at 30° C. and left overnight. Analysis of plates consisted of isolating any strains that exhibited resistance to Octodrine at 10 mM concentration. Resistance was noted by the ability of the *Candida* cells and the subsequent drug-treated spot to lack a halo.

Mammalian cell culture, drug treatment, and survival assay: RAW264.7 mouse macrophage cells were maintained in DMEM (Dulbecco's Modified Eagle Medium, Sigma-Aldrich) supplemented with 10% FBS (fetal bovine serum, Bioexpress) and 100 µg/mL penicillin and 100 µg/mL streptomycin. RAW264.7 cells (10,000 per well) were seeded in 96-well plates (100 µL/well) 24 hours before the assay. During the assay, 1 µl of 10 mM drug was added to 100 µl of cell-containing media. Two-fold serial dilutions of the media were performed. Cells were treated with drugs for 24 hours, and determination of cell viability by 3-(4,5-dimethylthiazol-2-yl)-2,5-diphenyltetrazolium bromide (MTT) assay was performed as described in Lu et al., 2004, *Proc Natl Acad Sci USA* 101:17246-17251, the entire content of which is herein incorporated by reference.

Each data point shown in the figure for MTT assays represents the average of results from at least two wells in each of at least two separate experiments. Cell viability is shown as the percentage of survivors obtained relative to untreated cells (100%).

Image Capture and Image Processing: All images were taken with an 8MP iSight camera with an aperture size of F2.4 and touch-to-focus capabilities. Images were standardized with a universal template to allow for direct comparison between images. Images are stock and unaltered by any graphics editing software.

This study was designed to test FDA-approved small molecules drugs for their antifungal properties, with the objective of reducing the cost and time necessary to develop much needed anti-*Candida albicans* therapies. This library consists of an FDA-approved, off-patent collection of 1,581 small molecules (10 mM) that are used as drugs for a variety of diseases: including infectious, neurodegenerative, psychiatric, cardiovascular diseases and cancer.

As disclosed herein, 15 out of 1,581 drugs displayed anti-*Candida* properties. This hit rate of 1% is higher than the typical hit rate of 0.1% reported for high-throughput screening of large libraries of small synthetic molecules. Presumably, a high hit rate was the result of using the Johns Hopkins Clinical Compound Library collection which consists only of approved drugs, while a random chemical library may contain numerous non-drug-like molecules.

Figure 6:
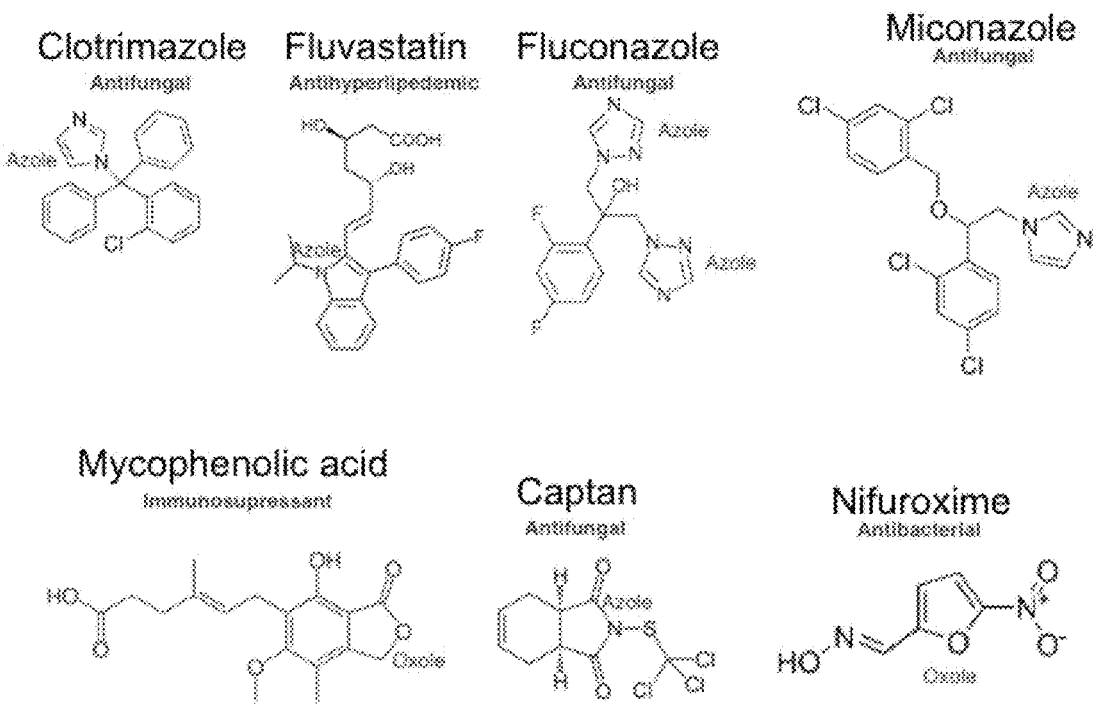
FIG. 6 shows the chemical structures of the 15 "hit" drugs from the screen shown in FIG. 1A and summarized in FIG. 1B, which were shown to have anti-*Candida albicans* activity, according to embodiments of the present invention.
Figure 6:
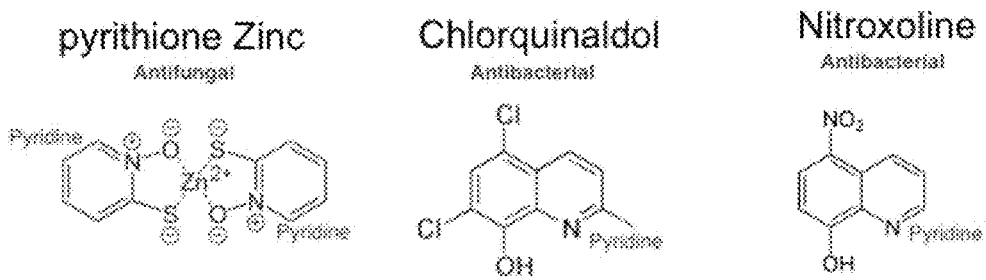

Overall, all drugs discovered in our study could be separated into three structural categories: five-membered heterocyclic compounds, such as azoles and oxoles, six-membered heterocyclic compounds (pyridines), and other structures (FIG. 6). The six antifungal compounds obtained as hits from the screen comprised three different chemical classes: azoles (Fluconazole, Captan, Clotrimazole, and Miconazole), pyridine (Pyrithione Zinc), and other structures (Antimycin A). Additionally, five antimicrobial/antiseptic compounds were identified to be effective at inhibiting *C. albicans* lawn formation. These compounds include general antiseptics and antibacterial antibiotics, and comprise three different chemical classes: oxoles (Nifuroxime), pyridines (Nitroxoline and Chlorquinaldole), and other structures (Octanoic acid and Benzethonium Chloride).

As disclosed herein, Octodrine, the FDA-approved decongestant, was the only drug in the screen that had not been previously established as an anti-fungal. Although the anti-*Candida* activity of Octodrine was mild on YPD, it displayed the best *Candida* growth inhibition on serum compared to other drugs (FIG. 1A). Octodrine also did not affect the sensitivity of mammalian macrophages (FIG. 5), indicative of a safe drug. The fact that no *C. albicans* mutants (FIG. 3) showed a decrease in sensitivity to Octodrine argues against the potential emergence of Octodrine-resistant *Candida* strains, which favors the usage of this drug as a new antifungal treatment against *Candida*. In addition, Octodrine is capable of killing Gram-positive as well as Gram-negative bacteria, (FIG. 4), making it a desirable broad-spectrum antimicrobial countermeasure.

While the present invention has been illustrated and described with reference to certain exemplary embodiments, those of ordinary skill in the art will understand that various modifications and changes may be made to the described embodiments without departing from the spirit and scope of the present invention, as defined in the following claims.

What is claimed is:

1. A method of inhibiting the proliferation of *Candida, Escherichia coli*, and/or *Bacillus*, comprising administering to a living organism having exposure to the fungus and/or bacteria, a therapeutic amount of an antimicrobial composition comprising Octodrine.

2. The method of claim 1, wherein the living organism is selected from the group consisting of mammals, birds, fish, and plants.

3. The method of claim 1, wherein the living organism is a human.

4. The method of claim 1, wherein the antimicrobial composition further comprises an excipient selected from the group consisting of vitamins, minerals, amino acids, fats, oils, and combinations thereof.

5. The method of claim 1, wherein the antimicrobial composition further comprises an additive selected from the group consisting of other antifungals, antibacterials, antibiotics, antimicrobials, antivirals, antiparasitic, and combinations thereof.

6. A method of treating *candidiasis* in a living organism, comprising administering to the living organism having the *candidiasis* a therapeutic amount of an antimicrobial composition comprising Octodrine.

7. The method of claim 6, wherein the antimicrobial composition further comprises an excipient selected from the group consisting of vitamins, minerals, amino acids, fats, oils, and combinations thereof.

8. The method of claim 6, wherein the antimicrobial composition further comprises an additive selected from the group consisting of other antifungals, antibacterials, antibiotics, antimicrobials, antivirals, antiparasitic, and combinations thereof.

9. A method of inhibiting the proliferation of *Candida, Escherichia coli*, and/or *Bacillus* in air, in water, and/or on a surface, comprising administering an effective amount of an antimicrobial composition comprising Octodrine to the air, the water, and/or the surface having *Candida, Escherichia coli*, and/or *Bacillus*.

10. The method of claim 9, wherein the surface is the surface of food.

11. The method of claim 9, wherein the water is drinking water.

12. A method of treating air, water, and/or a surface, comprising administering an effective amount of antimicrobial composition comprising Octodrine in an amount effective to inhibit growth of *Candida, Escherichia coli*, and/or *Bacillus*.

* * * * *